US006115637A

United States Patent [19]
Lennox et al.

[11] Patent Number: 6,115,637
[45] Date of Patent: Sep. 5, 2000

[54] MICROCURRENT THERAPEUTIC TECHNIQUE FOR TREATMENT OF RADIATION TOXICITY

[75] Inventors: Arlene Lennox, Elburn; Sandra Funder, Crown Point, both of Ill.

[73] Assignee: Universities Research Association, Inc., Washington, D.C.

[21] Appl. No.: 09/218,759

[22] Filed: Dec. 22, 1998

[51] Int. Cl.[7] .................................................. A61N 1/32
[52] U.S. Cl. .............................................................. 607/68
[58] Field of Search ................................. 607/66, 68, 69, 607/70, 71, 72, 73, 74

[56] References Cited

U.S. PATENT DOCUMENTS 3,842,841  10/1974  Brighton et al. .

OTHER PUBLICATIONS

Talal, et al., "The clinical effects of electrostimulation on salivary function of Sjogren's syndrome patients," *Rheumatology International,* 12:43–45 (1992).

Thakkar, "Researchers make slow headway in managing dry mouth," *Journal of the National Cancer Institute,* 89(18):1337–1338 (Sep. 1997).

Weber, et al., "The effects of three modalities on delayed onset muscle soreness," Journal of Orthopaedic and Sports Physical Therapy, 20(5):236–242 (Nov. 1994).

Yuan, "Spontaneous cure in a case of terminal progressive multifocal leukoencephalopathy (PML) in an HIV positive patient after the use of ozone, a vitamin–mineral nutrient program, neurolinguistic programming (NLP) and silva mind control (SMC) techniques as well as advanced applications of the Electro–Accuscope," *Raum & Zeit: The New Dimension in Scientific Research,* 2(6):1–6 (1991).

Altman, Cell channel finding earns Nobel prize, *New York Times Medical Science,* (Oct. 8, 1991).

Bauer, "Electrical treatment of severe head and neck cancer pain," *Arch Otolaryngol,* 109:382–383 (1983).

Bertolucci, et al., "Clinical Comparative Study of Microcurrent Electrical Stimulation of Mid–Laser and Placebo Treatment in Degenerative Joint Disease of the Temporomandibular Joint," *The Journal of Craniomandibular Practice,* 13(2):116–120 (1995).

Boswell, "Neuroelectric therapy eliminates xerostomia during radiotherapy—a case history," *Medical Electronics,* 115:105–107 (Feb. 1989).

Boswell, et al., "Noninvasive electrical stimulation for the treatment of radiotherapy side effects," *American Journal of Electromedicine,*1(3) (1985).

Burr, "Selected reprints of published articles on the bioelectrical potentials of living creatures and the environment 1935–1937," Natural Energy Works, P.O. Box 864, El Cerrito, CA 94530 (date unknown).

Byl, et al., "Pulsed Microamperage Stimulation: A Controlled Study of Healing of Surgically Induced Wounds in Yucatan Pigs," *Physical Therapy* 74(3):201–203 (Mar. 1994).

Curl, et al., "The use of infra–red thermography to examine the effects of the Electro–Accuscope in treating myofascial trigger points," *Network–Electrix,* (Sep. 1987).

(List continued on next page.)

*Primary Examiner*—Scott M. Getzow
*Attorney, Agent, or Firm*—McAndrews, Held & Malloy, Ltd.

[57] ABSTRACT

The present technique provides a method of remediating the toxicities associated with radiation therapy. A conductive gel is applied to the affected bodily area. A sinusoidally pulsed biphasic DC current is then applied to the affected bodily area using at least one electrode. The electrode is manipulated using active tactile manipulation by for a predetermined time and the frequency of the sinusoidally pulsed biphasic DC current is decreased during the course of the treatment. The method also includes applying a spiked pulsed biphasic DC current to the affected bodily area using at least one electrode. This electrode is also manipulated using active tactile manipulation by for a predetermined time and the frequency of the spiked pulsed biphasic DC current is also decreased during the course of the treatment.

24 Claims, 1 Drawing Sheet

OTHER PUBLICATIONS

De La Porte, et al., "Lumbosacral Spinal Fibrosis (Spinal Arachnoiditis)," *Spine,* 8(6):593–603 (1983).

H'Doubler, "The treatment of post–polio syndrome with electrostimulation of auricular acupuncture points; an evaluation of twelve patients," *American Journal of Acupuncture,* 22(1):15–21 (1994).

Johnson, et al., "Oral pilocarpine for post–irradiation xerostomia in patients with head and neck cancer," *New England Journal of Medicine,* 329:390–395 (Aug. 1993).

King, et al., "Electrotherapy and hyperbaric oxygen: Promising treatments for postradiation complications," *The Journal of Prosthetic Dentistry,* 62(3):331–334 (Sep. 1989).

Lucero, "The Electro–Acuscope/Myopulse System: Impedance–monitoring microamperage therapy for tissue repair," *Rehab Management,* 4(3) (Apr. 1993).

Meyer, "Double–blind comparative study of the Electro–Accuscope and placebo effect in short term treatment of the chronic back pain patient," *California Health Review 2(1)* (1983).

Morell, "The MORA Concept," (date unknown).

Noto, et al., "Comparative study of micro–amperaqge neural stimulation and conventional therapy modalities," (1982).

Probst, "Spinal Cord Stimulation in 112 Patients with Epi–Intradural Fibrosis Following Operation for Lumber Disc Herniation," *Acta Neurochirugica,* 107:147–151 (1990).

Sartori, "New hope for multiple sclerosis with the multimodal comprehensive life science universal (LSU) treatment program," *Raum & Zeit: The New Dimension in Scientific Research,* 2(6):35–47.

6,115,637

MICROCURRENT THERAPEUTIC TECHNIQUE FOR TREATMENT OF RADIATION TOXICITY

This invention was made with Government support under Contract No. DE-AC02-76CH03000 awarded by the United States Department of Energy. The Government has certain rights in the invention.

FIELD OF THE INVENTION

The present invention relates to radiation therapy and more particularly concerns a microcurrent therapeutic technique for relieving the radiation toxicities associated with radiation therapy.

BACKGROUND OF THE INVENTION

Radiation therapy is the use of penetrating beams of radiation to treat disease. Various forms of radiation therapy, including photon, electron, and neutron radiation, are used on a daily basis in the United States and throughout the world. One major use of radiation therapy is the treatment of cancerous tumors. The basic effect of radiation therapy is to destroy the ability of cells to divide and grow by damaging their DNA strands. This effect is useful in killing cancerous cells, but it has the major disadvantage of damaging healthy tissue as well. As a result, the patient may be required to live with debilitating side effects including limb or organ swelling, thickening and hardening of tissue, and chronic or constant pain.

The deleterious side effects produced in the patient as a result of radiation therapy are known as radiation toxicities. Radiation toxicities are associated with any ionizing radiation treatment and include fibrotic tissue (scar tissue), xerostomia (loss of salivary function), trismus (closure of the jaw), radiation proctitis (inflammation of the rectum), limited range of motion, loss of motor coordination, edema (swelling), and lymphedema (swelling resulting from obstruction of the lymphatic vessels or lymph nodes). Unfortunately, the side effects associated with radiation therapy are progressive in most cases and they tend to worsen over time. Current practice for treating late side effects of cancer treatment include physical therapy, massage, exercise, and drugs, such as diuretics, pain killers, steroids, and saliva inducers. However, in most cases, these treatments provide the patient with only minimal relief, and the patient may be required to live with the debilitating side effects of radiation therapy.

Thus, a need has long existed in the industry for a method of providing a more effective method of alleviating the radiation toxicities associated with radiation therapy.

It is therefore an object of the present invention to provide a method that alleviates the radiation toxicities associated with radiation therapy.

It is a further object of the invention to provide a method for pre-treating a patient to avoid the radiation toxicities associated with radiation therapy.

SUMMARY OF THE INVENTION

One or more of the foregoing objects is met in whole or in part by a microcurrent therapeutic technique for relieving the radiation toxicities associated with radiation therapy. The method includes the steps of applying a sinusoidally pulsed biphasic DC current to the affected bodily area using active tactile manipulation by at least one electrode for a predetermined time and decreasing the frequency range of the current from a higher frequency to a lower frequency during the course of the treatment. The method also includes applying a spiked pulsed biphasic DC current to the affected bodily area using active tactile manipulation by at least one electrode for a predetermined time and decreasing the frequency range of the current from a higher frequency to a lower frequency during the course of the treatment. Additionally, a conductive gel may be applied to the affected bodily area. Preferably, the method will be performed about twice per day for about three to five days.

Both the electrode used to apply the sinusoidally pulsed biphasic DC current and the electrode used to apply the spiked pulsed biphasic DC current may be on a probe. The sinusoidally pulsed biphasic DC current may be adjusted from a higher frequency of about 100 Hz to a lower frequency of about 10 Hz, and the spiked pulsed biphasic DC current may be adjusted from a higher of about 320 Hz to a lower frequency of about 10 Hz. Additionally, the sinusoidally pulsed biphasic DC current may be about 600 microamperes, and the spiked pulsed biphasic DC current may be about 600 microamperes. Preferably, both the sinusoidally pulsed biphasic DC current and the spiked pulsed biphasic DC current will be applied for approximately 20 minutes.

Preferably, the size of the probes used to apply both the sinusoidally pulsed biphasic DC current and the spiked pulsed biphasic DC current will be adjusted to achieve maximum skin contact over the largest possible affected bodily area. The probes used to apply both currents may be selected for treating larger affected bodily areas, smaller affected bodily areas, or crevicular areas. Additionally, both probes may be cylindrical in shape or may be suitable for intra-oral manipulation.

DETAILED DESCRIPTION OF PREFERRED EMBODIMENTS

Figure 1:
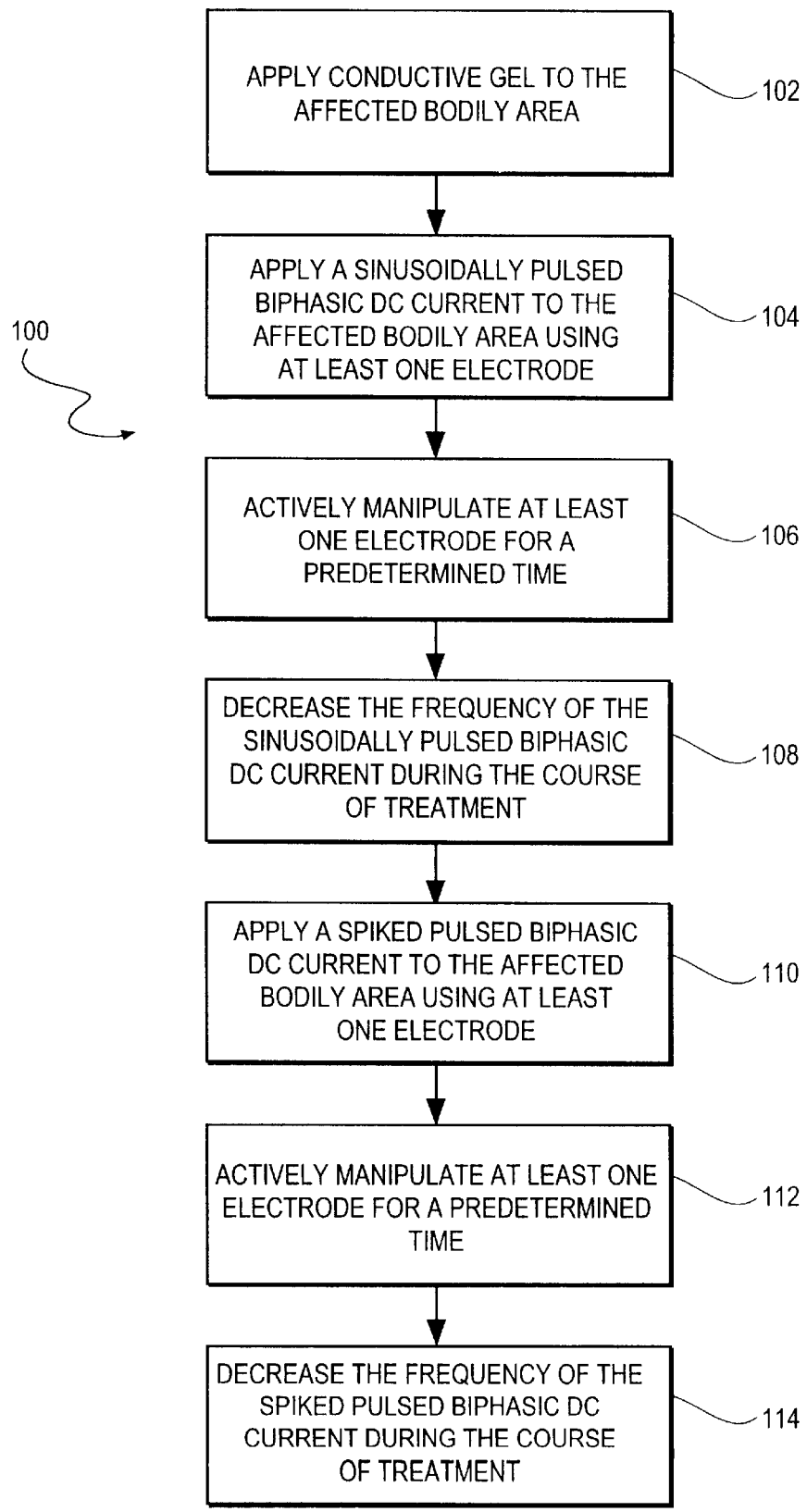
FIG. 1 is a flow diagram of the steps for relieving the radiation toxicities associated with radiation therapy using a microcurrent therapeutic technique in accordance with one embodiment of the present microcurrent therapeutic technique.

Turning to FIG. 1, a flow diagram 100 shows the preferred steps for treating radiation therapy toxicities in accordance with one embodiment of the present microcurrent therapeutic technique. The illustrated method includes a first application step 102, a second application step 104, a first manipulation step 106, and a first decreasing step 108. Also shown are a third application step 110, a second manipulation step 112, and a second decreasing step 114.

As illustrated in FIG. 1, a conductive gel is first applied to the affected bodily area (step 102). A sinusoidally pulsed biphasic DC current is then applied to the affected bodily area using at least one electrode (step 104). For example, the sinsoidally pulsed current will be applied using the Myopulse, which is a device available through Electro-Medical of Fountain Valley, Calif. Preferably, the sinusoidally pulsed biphasic DC current will first be applied to the lymphatic system, which corresponds to the affected bodily area. The electrode used to apply the sinusoidally pulsed biphasic DC current may be on a probe. The size of the probe may be adjusted to achieve maximum skin contact over the affected bodily area and will preferably be selected for treating larger affected bodily areas, smaller affected bodily areas, or crevicular areas. Additionally, the probe used to apply the sinusoidally pulsed biphasic DC current may be cylindrical in shape or it may be suitable for intra-oral manipulation.

At least one of the electrodes should be actively manipulated for a predetermined time (step 106). The time that the sinusoidally pulsed biphasic DC current is applied may be, for example, approximately 20 minutes. The frequency of the sinusoidally pulsed biphasic DC current should be decreased during the course of treatment (step 108). For example, the sinusoidally pulsed biphasic DC current may be adjusted from a higher frequency of about 100 Hz to a lower frequency of about 10 Hz. Additionally, although the sinusoidally pulsed biphasic DC current will preferably be about 600 microamperes, the patient should not be allowed to experience pain during the treatment in any case.

A spiked pulsed biphasic DC current should then be applied to the affected bodily area using at least one electrode (step 110). The spiked pulsed biphasic DC current may be applied, for example, using the Electro-Acuscope, which is available through Electro-Medical of Fountain Valley, Calif. The electrode used to apply the spiked pulsed biphasic DC current may be on a probe, and the probe may be selected substantially as was discussed above. At least one of the electrodes should be actively manipulated for a predetermined time (step 112) during the application of the spiked pulsed biphasic DC current. The spiked pulsed biphasic DC current may also be applied, for example, approximately 20 minutes. As was discussed above with respect to the sinusoidally pulsed biphasic DC current, the frequency of the spiked pulsed biphasic DC current should be decreased during the course of treatment (step 114). For example, the spiked pulsed biphasic DC current may be adjusted from a higher frequency of about 320 Hz to a lower frequency of about 10 Hz. The spiked pulsed biphasic DC current will preferably be about 600 microamperes. However, as was the case with respect to the sinusoidal pulsed biphasic DC current, the patient should not be allowed to experience pain during the treatment.

Preferably, the microcurrent therapeutic technique for relieving the radiation toxicities associated with radiation therapy will be performed about twice per day for about three to five days.

The present microcurrent therapeutic technique provides a method that alleviates the debilitating radiation toxicities associated with radiation therapy, including fibrotic tissue, xerostomia, trismus, radiation proctitis, limited range of motion, loss of motor coordination, edema, and lymphedema. The present technique provides greater pain relief than other methods for treating the late side effects of cancer treatment, thus allowing the patient to have a higher quality of life. The method embodied in the present technique may also be used for pre-treating a patient to avoid the radiation toxicities associated with radiation therapy.

While particular elements, embodiments and applications of the present invention have been shown and described, it will be understood, of course, that the invention is not limited thereto since modifications may be made by those skilled in the art, particularly in light of the foregoing teachings. It is therefore contemplated by the appended claims to cover such modifications as incorporate those features that come within the spirit and scope of the invention.

What is claimed is:

1. A method of remediating toxicities affecting a bodily area having undergone radiation therapy, the method comprising the steps of:

(a) applying a sinusoidally pulsed biphasic DC current to at least a portion of an affected bodily area using active tactile manipulation by at least one first electrode for a first predetermined time;

(b) adjusting the frequency range of said sinusoidally pulsed biphasic DC current from a higher frequency to a lower frequency;

(c) applying a spiked pulsed biphasic DC current to at least a portion of said affected bodily area using active tactile manipulation of at least one second electrode for a second predetermined time;

(d) adjusting the frequency range of said spiked pulsed biphasic DC current from a higher frequency to a lower frequency.

2. The method of claim 1 wherein steps (a) through (d) are preformed sequentially.

3. The method of claim 1 further comprising performing steps (a) through (d) about twice per day for about three to five days.

4. The method of claim 1 further comprising applying a conductive gel to said affected bodily area.

5. The method of claim 1 wherein said first electrode is on a probe.

6. The method of claim 5 wherein the size of said first probe is selected to achieve maximum skin contact over the affected bodily area.

7. The method of claim 5 wherein the size of said first probe is suitable for treating larger affected bodily areas.

8. The method of claim 5 wherein the size of said first probe is suitable for treating smaller affected bodily areas.

9. The method of claim 5 wherein said first probe is suitable for treating crevicular areas.

10. The method of claim 5 wherein said first probe is cylindrical in shape.

11. The method of claim 5 wherein said first probe is suitable for intra-oral manipulation.

12. The method of claim 1 wherein said second electrode is on a probe.

13. The method of claim 12 wherein the size of said second probe is selected to achieve maximum skin contact over the affected bodily area.

14. The method of claim 12 wherein the size of said second probe is suitable for treating larger affected bodily areas.

15. The method of claim 12 wherein the size of said second probe is suitable for treating smaller affected bodily areas.

16. The method of claim 12 wherein said second probe is suitable for treating crevicular areas.

17. The method of claim 12 wherein said second probe is cylindrical in shape.

18. The method of claim 12 wherein said second probe is suitable for intra-oral manipulation.

19. The method of claim 1 wherein said sinusoidally pulsed biphasic DC current is adjusted from a higher frequency of about 100 Hz to a lower frequency of about 10 Hz.

20. The method of claim 1 wherein said spiked pulsed biphasic DC current is adjusted from a higher of about 320 Hz to a lower frequency of about 10 Hz.

21. The method of claim 1 wherein said sinusoidally pulsed biphasic DC current is about 600 microamperes.

22. The method of claim 1 wherein said spiked pulsed biphasic DC current is about 600 microamperes.

23. The method of claim 1 wherein said first predetermined time is approximately 20 minutes.

24. The method of claim 1 wherein said second predetermined time is approximately 20 minutes.

* * * * *

UNITED STATES PATENT AND TRADEMARK OFFICE
CERTIFICATE OF CORRECTION

PATENT NO.   : 6,115,637
DATED        : September 5, 2000
INVENTOR(S)  : Arlene Lennox and Sandra Funder It is certified that error appears in the above-identified patent and that said Letters Patent is hereby corrected as shown below:

<u>Title page,</u>
Item [56], References Cited, under OTHER PUBLICATIONS, please correct a typographical error in the reference authored by Noto, et al. The corrected title is as follows: -- Comparative study of micro-amperage neural stimulation and conventional therapy modalties. --
Item [75], Inventor, the corret inventor address information is as follows:
-- Arlene Lennox, Elburn, IL
Sandra Funder, Crown Point, IN Signed and Sealed this Sixteenth Day of July, 2002

Attest:

JAMES E. ROGAN
*Attesting Officer*          *Director of the United States Patent and Trademark Office*